United States Patent
Hall et al.

(10) Patent No.: US 11,378,438 B2
(45) Date of Patent: Jul. 5, 2022

(54) FLUID MEASUREMENT INTERFACE SYSTEMS AND METHODS

(71) Applicant: Simmonds Precision Products, Inc., Vergennes, VT (US)

(72) Inventors: Robbie William Hall, Charlotte, VT (US); James Christopher Averill, North Ferrisburgh, VT (US)

(73) Assignee: Simmonds Precision Products, Inc., Vergennes, VT (US)

(*) Notice: Subject to any disclaimer, the term of this patent is extended or adjusted under 35 U.S.C. 154(b) by 509 days.

(21) Appl. No.: 16/267,035

(22) Filed: Feb. 4, 2019

(65) Prior Publication Data

US 2019/0285458 A1 Sep. 19, 2019

Related U.S. Application Data

(63) Continuation-in-part of application No. 15/924,806, filed on Mar. 19, 2018.

(51) Int. Cl.
*G01F 23/80* (2022.01)
*G01F 23/263* (2022.01)
(Continued)

(52) U.S. Cl.
CPC ............ *G01F 23/804* (2022.01); *G01F 23/22* (2013.01); *G01F 23/263* (2013.01);
(Continued)

(58) Field of Classification Search
CPC .... G01F 23/0076; G01F 23/22; G01F 23/292; G01N 27/221
See application file for complete search history.

(56) References Cited

U.S. PATENT DOCUMENTS 5,298,887 A * 3/1994 Pepping ............... B22D 11/186
164/450.1
7,825,816 B2 11/2010 Jarvie et al.
(Continued)

FOREIGN PATENT DOCUMENTS

DE 3322244 A1 * 1/1985 ............. H02H 9/008
EP 0056135 A1 * 12/1981
(Continued)

OTHER PUBLICATIONS

Mary Attenborough, Parity Bit, Mathematics for Electrical Engineering and Computing, 2003 (Year: 2003).*
(Continued)

*Primary Examiner* — Matthew G Marini
(74) *Attorney, Agent, or Firm* — Locke Lord LLP; Scott D. Wofsy; Alicia J. Carroll (57) ABSTRACT

A fluid measurement system includes a signal processor and a processing system. The signal processor is configured and adapted to produce a serial word that is indicative of a fluid characteristic that is configured to be communicated externally of the signal processor. The processing system is operatively connected to the signal processor to read the serial word and decode the serial word. A method for transmitting a fluid characteristic between a sensor system and a processing system includes producing a serial word that is indicative of a fluid characteristic value with a signal processor. The method includes transmitting the serial word externally of the signal processor. The method includes reading and decoding the serial word with a processing system to determine the fluid characteristic value.

17 Claims, 6 Drawing Sheets

(51) Int. Cl.
  *G01N 27/22* (2006.01)
  *G01N 29/024* (2006.01)
  *G01F 23/292* (2006.01)
  *G01N 33/22* (2006.01)
  *G01F 23/22* (2006.01)
  *H03M 5/02* (2006.01)

(52) U.S. Cl.
  CPC ......... *G01F 23/292* (2013.01); *G01N 27/221* (2013.01); *G01N 29/024* (2013.01); *G01N 33/22* (2013.01); *H03M 5/02* (2013.01); *G01N 2291/02818* (2013.01)

(56) References Cited

U.S. PATENT DOCUMENTS

| | | |
|---|---|---|
| 9,109,940 B2 | 8/2015 | Bahorich et al. |
| 9,910,025 B2 | 3/2018 | Kumar et al. |
| 2009/0013798 A1 | 1/2009 | Hocker |
| 2017/0351634 A1* | 12/2017 | Fustos .................. G06F 13/4221 |

FOREIGN PATENT DOCUMENTS

| | | |
|---|---|---|
| EP | 3205987 A1 | 8/2017 |
| EP | 3220175 A1 | 9/2017 |
| GB | 2033091 A | 5/1980 |
| WO | 84/01428 A1 | 4/1984 |
| WO | 99/32856 A1 | 7/1999 |
| WO | 03/073139 A2 | 9/2003 |
| WO | 2013/142717 A2 | 9/2013 |

OTHER PUBLICATIONS

Machine translation of August, (Year: 1985).*
Puttmer, A., et al., "Ultrasonic Density Sensor for Liquids", internet article, Jan. 31, 2000, XP002793595, URL: https://eeexplore.ieee.org/document/818751.
Extended European Search Report dated Sep. 4, 2019, issued during the prosecution of European Patent Application No. 19163468.2.
Communication Pursuant to Article 94(3) EPC dated Nov. 23, 2020, issued during the prosecution of European Patent Application No. 19163468.2.

* cited by examiner

FLUID MEASUREMENT INTERFACE SYSTEMS AND METHODS

CROSS-REFERENCE TO RELATED APPLICATIONS

This application is a continuation-in-part of U.S. patent application Ser. No. 15/924,806, filed Mar. 19, 2018, the contents of which are incorporated by reference herein in their entirety.

BACKGROUND

1. Field

The present disclosure relates to remote fluid sensors, and more particularly to interfaces between remote fluid sensors, such as a fuel dielectric sensor within an integrated density compensation system, and a processing system, such as a fluid characterization system.

2. Description of Related Art

Aircraft use a variety of sensing devices for measuring the height of fuel in tanks and fluid characteristics of the fuel such as density, temperature and fuel dielectric. A processing system receives the fluid characteristic data and fluid level data. This fluid characteristic data is then used to compensate the fluid level measurements to determine the fuel mass. Aviation fuel level sensors use a capacitive sensing device that produces a signal representative of the fuel level as a result of the dielectric value of the fuel immersing the sensor. Because the density and/or dielectric value of fuel can vary with temperature, fuel type, and other parameters, fuel density and dielectric value are also measured utilizing separate density and dielectric detectors.

These characterization value measurements are then used to compensate the measurements of fuel level made by the fuel dielectric level sensors which are located at various points in the fuel tanks. Therefore, a pair of detectors is typically used to provide the characterization of fuel in a tank, one measuring fuel density and the other measuring fuel dielectric value. Power and signal cables typically connect each detector to a central processing system, e.g. an avionics computer, where the fuel mass is calculated by applying the density and dielectric values to the inputs from the various fuel level detectors. The signal cables connecting each dielectric and density detector are typically shielded to reduce electromagnetic interference that could otherwise degrade the signals. An aircraft typically has a fuel tank in each wing, and one or more fuel tanks located in the fuselage. For redundancy, each fuel tank may have multiple pairs of fuel dielectric and density detectors. Accordingly, numerous cables are routed through fuel tanks to provide accurate fuel level measurements in the various fuel tanks on an aircraft, thereby contributing to the weight of the aircraft. Moreover, these cables contribute to the cost of an aircraft during construction, and also during maintenance when cables may require removal and replacement. Power and signal cables typically connect each sensing device to the processing system, where the fuel mass is calculated by applying the density and dielectric values to the inputs from the various fuel level sensors.

Such conventional methods and systems have generally been considered satisfactory for their intended purpose. However, there is still a need in the art for improved interfaces between the processing system and various sensing devices. The present disclosure provides a solution for this need.

SUMMARY

A fluid measurement system includes a signal processor and a processing system. The signal processor is configured and adapted to produce a serial word that is indicative of a fluid characteristic that is configured to be communicated externally of the signal processor. The processing system is operatively connected to the signal processor to read the serial word and decode the serial word.

In accordance with some embodiments, the serial word is representative of at least one of a density or a capacitance of a fluid. The serial word can include a plurality of bits. Each bit can be a 1 MHz bit cluster. Each 1 MHz bit cluster can include a plurality of 1 MHz pulses, e.g. ranging from 4-8 pulses. The plurality of bits can include a start bit, a plurality of data bits, and a parity bit.

The system can include a power interface between the signal processor and the processing system. The processing system can include an intrinsically safe power source and a current limiter. The current limiter can be between the intrinsically safe power source and the power interface. The processing system can include a velocity of sound signal conditioner to read and decode the serial word. The system can include a two-conductor wire pair between the signal processor and the velocity of sound signal conditioner.

In accordance with another aspect, a method for transmitting a fluid characteristic between a sensor system and a processing system includes producing a serial word that is indicative of a fluid characteristic value with a signal processor. The method includes transmitting the serial word externally of the signal processor. The method includes reading and decoding the serial word with a processing system to determine the fluid characteristic value.

In accordance with some embodiments, producing the serial word includes generating a plurality of bits with the signal processor. The plurality of bits can include a start bit, a plurality of data bits, and a parity bit. Each bit can be a 1 MHz bit cluster, and/or each bit cluster can include a plurality of 1 MHz pulses, e.g. ranging from 4-8 pulses. The method can include limiting current to 50 mA or less with a current limiter between an intrinsically safe power source and a power interface. The reading and decoding of the serial word can be done by a velocity of sound signal conditioner of the processing system. The method can include disabling a velocity of sound transmit function of the velocity of sound signal conditioner. Transmitting the serial word externally can include wirelessly transmitting the serial word from the signal processor to the processing system.

These and other features of the systems and methods of the subject disclosure will become more readily apparent to those skilled in the art from the following detailed description of the embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE EMBODIMENTS

Reference will now be made to the drawings wherein like reference numerals identify similar structural features or aspects of the subject disclosure. For purposes of explanation and illustration, and not limitation, a partial view of an exemplary embodiment of a fluid measurement system having a sensor system and a processing system constructed in accordance with the disclosure is shown in FIG. 4 and is designated generally by reference character 100. Other embodiments of fluid measurement systems and for transmitting data between a sensor system and a processing system in accordance with the disclosure, or aspects thereof, are provided in FIGS. 1A-3 and 5-6, as will be described. The systems and methods described herein can be used in aviation fuel sensor systems to incorporate integrated densitometer and dielectric measurement systems with an existing fuel measurement processor having a velocity of sound processor to determine the fuel mass with increased accuracy and minimal hardware modifications. This permits easier install, reduced cost and minimal downtime.

Figures 1A, 1B:
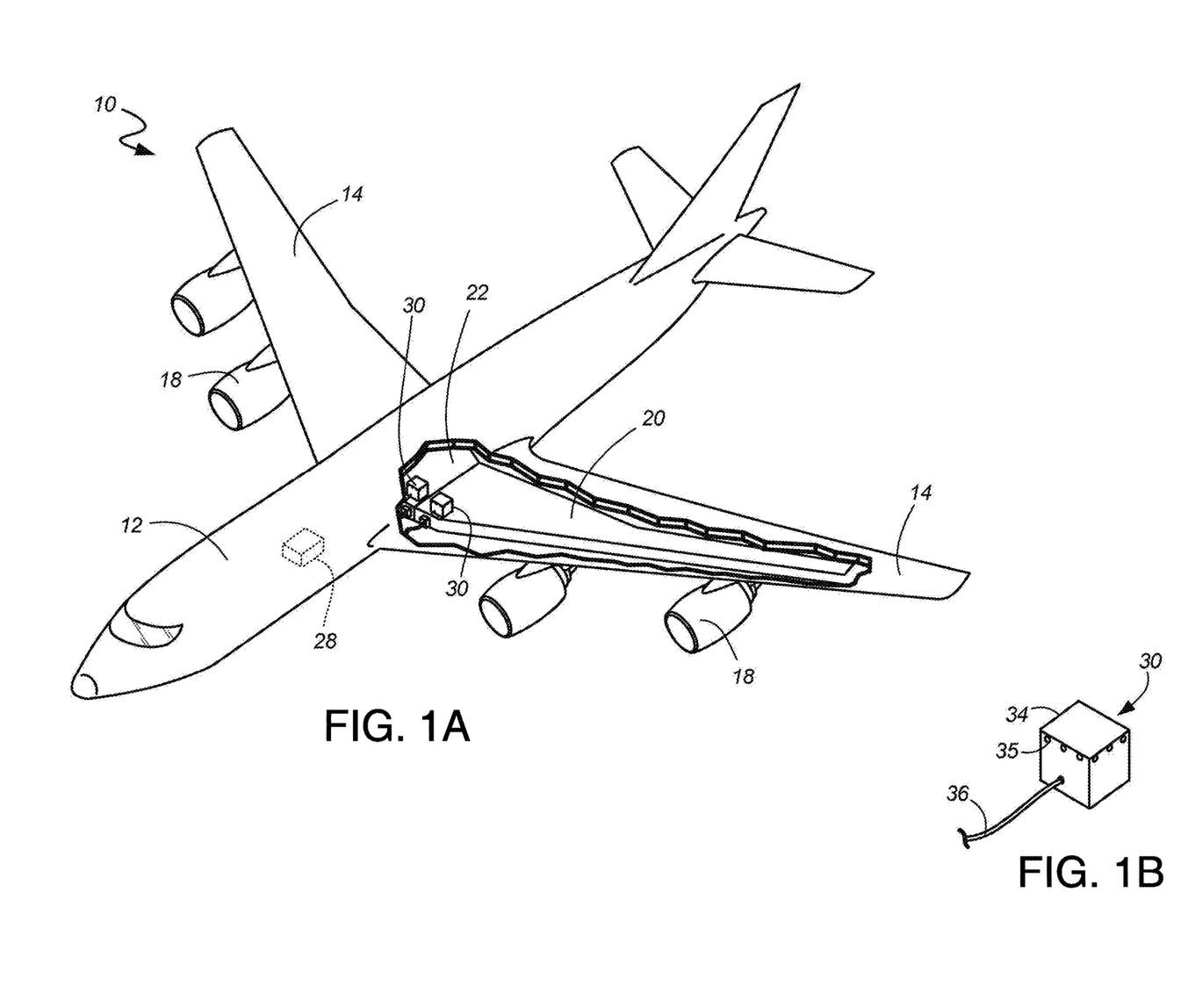
FIG. 1A is a perspective view of an aircraft showing the integrated densitometer-compensator.
FIG. 1B is a perspective view of the integrated densitometer-compensator.

FIG. 1A is a perspective view illustrating a portion of the fuel storage tanks onboard an aircraft. Shown in FIG. 1A is aircraft 10, fuselage 12, wings 14, engines 18, wing fuel tank 20, center fuel tank 22, avionics computer 28, and integrated densitometer-compensators 30. Aircraft 10 is an example of an aircraft in which integrated densitometer-compensators 30 may be employed for fuel density and dielectric value measurement. In the embodiment illustrated in FIGS. 1A-3, aircraft 10 has fuselage 12, two wings 14, and four engines 18. Fuselage 12 encloses the payload area of aircraft 10, typically consisting of passengers and/or cargo. Avionics computer 28 is a component in the overall instrumentation and control system of aircraft 10. For sake of simplicity in illustration, only one avionics computer 28 is depicted and interconnecting wires, cables, instrumentation systems, and the like, are not shown. As used in this disclosure, avionics computer 28 can also be called a remote computing device. Moreover, for simplicity in illustration, the various fuel level sensors that are located in wing fuel tanks 20 and center fuel tank 22 are not shown. Operating personnel, instrumentation, and control systems are also contained within fuselage 12. Those who are skilled in the art of aircraft instrumentation are familiar with the various avionics systems that may be located onboard aircraft 10. Wings 14 provide aerodynamic lift for airplane 10, while also holding engines 18. Engines 18 consume fuel to create thrust for airplane 10. Wing fuel tanks 20 and center fuel tank 22 hold fuel, which is consumed by engines 18.

Wing fuel tank 20 and center fuel tank 22 are exemplary of a plurality of fuel tanks that may be located in aircraft 10. Those who are skilled in the art of aircraft construction are familiar with the locations of various fuel tanks that may be located therein. For simplicity in illustration, one integrated densitometer-compensator 30 is shown in left wing fuel tank 20 and one integrated densitometer-compensator 30 is shown in center fuel tank 22. In a typical embodiment, each wing fuel tank 20 can have one or more integrated densitometer-compensators 30. Additionally, aircraft 10 can contain one or more center fuel tanks 22, with each center fuel tank 22 having an integrated densitometer-compensator 30.

Prior to flying, various fuel tanks within aircraft 10 may be filled with fuel which is to be consumed by engines 18 during flight. Prior to and during flight, crew members and/or systems aboard aircraft 10 can obtain knowledge of the inventory of fuel that exists in each of the various fuel tanks to calculate the mass and mass distribution of fuel stored throughout aircraft 10. Obtaining an accurate knowledge of the mass and mass distribution of fuel within aircraft 10 helps crew members determine take-off and landing parameters, calculate flying range, and adjust trim and balance, for example. In some embodiments, aircraft 10 may be refueled during flight. The fuel density and dielectric value can change with flight conditions and/or with each refueling. Crew members and/or systems aboard aircraft 10 may obtain knowledge of the inventory of fuel in each of the various fuel tanks during the refueling operation and after the completion of the refueling operation. Accordingly, systems aboard aircraft 10 require in-tank sensing of fuel density and dielectric value to perform the proper fuel mass calculations from the various fuel tank level sensors (not shown).

FIG. 1B is a perspective view of integrated densitometer-compensator 30 shown in FIG. 1A. Shown in FIG. 1B are integrated densitometer-compensator 30, chassis 34, vent ports 35, and interface cable 36. Most components of integrated densitometer-compensator 30 are located within chassis 34, and will be described in FIGS. 2 and 3. Fuel density measurement, dielectric value measurement, and signal processing takes place onboard integrated densitometer-compensator 30, requiring only one external power connection and one communication link to avionics computer 28. Accordingly, interface cable 36 carries power from avionics computer 28 to integrated densitometer-compensator 30, as well as a signal representing the fuel density and dielectric value from integrated densitometer-compensator 30 to avionics computer 28. The power and signal carried by interface cable 36 will be described in greater detail in FIG. 3.

With continued reference to FIG. 1B, chassis 34 is a box-like structure that encloses the other primary components of integrated densitometer-compensator 30. Several embodiments are available for the design of chassis 34, including a solid structure, a cage-like structure, or a mesh-like structure. If a solid structure is used, vent ports 35 can be included on chassis 34 to allow for air to escape when chassis 34 is covered by fuel. Vent ports 35 can also be used to allow for circulation of fuel through chassis 34, so that the density and dielectric value of the fuel being measured by integrated densitometer-compensator 30 is representative of the surrounding fuel.

In an embodiment, chassis 34 is an electrically conductive enclosure, thereby shielding the interior components of integrated densitometer-compensator 30 against electromagnetic interference (EMI). Non-limiting examples of the materials from which chassis 34 can be constructed include steel, aluminum, aluminum alloys, brass, and other metals. In an alternative embodiment, chassis 34 can be constructed of a material that does not provide EMI shielding to interior components. For example, in these alternative embodiments, chassis 34 can be constructed of plastic, fiberglass, or a composite material. In this alternative embodiment, it may be necessary to provide EMI shielding around internal components of integrated densitometer-compensator 30. In other embodiments, EMI shielding may not be necessary on integrated densitometer-compensator 30.

Figure 2:
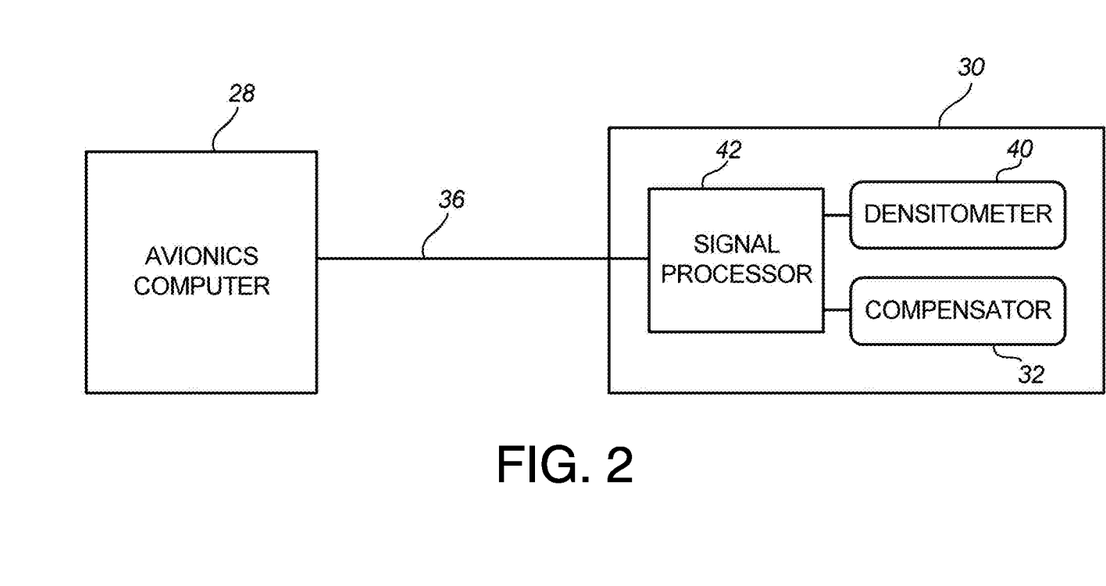
FIG. 2 is a block diagram of the integrated densitometer-compensator interface configuration.

FIG. 2 is a block diagram of the integrated densitometer-compensator interface configuration. Shown in FIG. 2 are avionics computer 28, integrated densitometer-compensator 30, compensator 32, densitometer 40, signal processor 42, and interface cable 36. As described in FIG. 1A, avionics computer 28 is a component in the overall instrumentation and control system of aircraft 10, and can also be described as a remote computing device. Compensator 32 produces a signal that is representative of the dielectric value of fuel immersing integrated densitometer-compensator 30. In some embodiments, compensator 32 can be described as an AC plate compensator because compensator 32 senses the dielectric value of fuel by applying an AC electrical measuring signal to the electrical capacitive plates within compensator 32, thereby detecting the electrical capacitive value of compensator 32. The principle of operation of compensator 32 is based on the measured electrical capacitive value changing in response to the change in the electrical dielectric value of the fuel.

Densitometer 40 provides a signal that represents the density of the fuel being measured by integrated densitometer-compensator 30, thereby providing density compensation to provide an accurate indication of the mass of fuel being measured in wing fuel tanks 20 and center fuel tank 22. As used in this disclosure, the terms "density" and "mass density" are equivalent. Compensating for the density and dielectric value of the fuel is beneficial in providing an accurate indication of the mass of the fuel. Because aircraft 10 can operate over a wide range of temperatures, the mass density of the fuel can vary, thereby requiring density compensation. The electrical dielectric value of fuel can also vary with fuel temperature, fuel density, and fuel formulation, thereby making it beneficial to provide fuel dielectric value compensation. In some embodiments, densitometer 40 can be described as a densitometer spool because densitometer 40 senses the density of the fuel by using a vibrating spool. The principle of operation of densitometer 40 is based on using a vibrating mechanical spool that is immersed in the fuel. Densitometer 40 includes an oscillator that that drives the mechanical spool at a mechanical resonant frequency. As the density of the fuel surrounding the mechanical spool of densitometer 40 varies, the mechanical spool's resonant frequency varies, and densitometer 40 produces an electrical signal that is representative of the fuel density.

In the embodiment illustrated in FIGS. 1A-3, avionics computer 28 is connected to integrated densitometer-compensator 30 by interface cable 36, with interface cable 36 providing power to integrated densitometer-compensator 30 and also transmitting data between avionics computer 28 and integrated densitometer-compensator 30. Signal processor 42 receives the electrical capacitance signal that is produced by compensator 32 and the fuel density signal that is produced by densitometer 40. Signal processor 42 produces a digital signal representative of the density and the dielectric value of fuel being measured by integrated densitometer-compensator 30. The digital signal is transmitted to avionics computer 28 by interface cable 36. In some embodiments, interface cable 36 can transmit digital signals in both directions between avionics computer 28 and integrated densitometer-compensator 30.

In the embodiment illustrated in FIGS. 1A-3, interface cable 36 transmits power to integrated densitometer-compensator 30. In some embodiments, interface cable 36 transmits electrical power to integrated densitometer-compensator 30. In other embodiments, interface cable 36 transmits optical power to integrated densitometer-compensator 30. In some embodiments, the transmission of power by interface cable 36 to integrated densitometer-compensator 30 is continuous or substantially continuous during operation of integrated densitometer-compensator 30. In other embodiments, the transmission of power by interface cable 36 to integrated densitometer-compensator 30 is intermittent during operation of integrated densitometer-compensator 30. In yet other embodiments, the transmission of power by interface cable 36 to integrated densitometer-compensator 30 may occur when integrated densitometer-compensator 30 is not providing data to avionics computer 28. For example, in some embodiments, integrated densitometer-compensator 30 can include an internal electrical energy storage system that is charged when integrated densitometer-compensator 30 is not transmitting data to avionics computer 28. Interface cable 36 and the power supply for integrated densitometer-compensator 30 will be discussed in greater detail in FIG. 3.

The integrated densitometer-compensator interface configuration shown in FIG. 2 is representative of the connection of integrated densitometer-compensator 30 on aircraft 10. As noted in FIG. 1A, wing fuel tanks 20 and center fuel tank 22 can each include one or more integrated densitometer-compensators 30. In some embodiments, all integrated densitometer-compensators 30 on aircraft 10 can be connected to a single avionics computer 28. In other embodiments, aircraft 10 can contain multiple avionics computers 28. In these other embodiments, the connection of integrated densitometer-compensators 30 to avionics computers 28 can be versatile, with the interface cable 36 of a particular integrated densitometer-compensator 30 being switchable between avionics computers 28. In other embodiments, integrated densitometer-compensators 30 can be daisy-chained together, with interface cable 36 from one integrated densitometer-compensator 30 being connected to another integrated densitometer-compensator 30, thereby allowing avionics computer 28 to communicate with and provide power to more than one integrated densitometer-compensator 30. In yet other embodiments, integrated densitometer-compensators 30 can be daisy-chained together with other sensors.

As described in more detail below related to the embodiment of system 100, integrated densitometer-compensator 30 produces a serial word that represents the density and dielectric value of fuel being measured by integrated densitometer-compensator 30. Accordingly, each individual integrated densitometer-compensator 30 can include a unique address, allowing for two or more integrated densitometer-compensators 30 to be daisy-chained together along a single interface cable 36. In other embodiments, integrated densitometer-compensator 30 can wirelessly transmit the serial word (including a unique address) to a wireless receiving device (not shown), which is connected to avionics computer 28. As used in this disclosure, "serial word" is used to describe a digital serial data stream being transmitted by integrated densitometer-compensator 30, with this data stream including digital representations of the density and dielectric value of fuel being measured by integrated densitometer-compensator 30. Under some operating conditions, integrated densitometer-compensator 30 can transmit a serial word that represents only the density or the dielectric value of the fuel. Under other operating conditions, integrated densitometer-compensator 30 can transmit a serial word that provides data other than the density or the dielectric value of the fuel. The "serial word" may also include a device address, checksum bits, and any other data, and it may be of any word size.

Figure 3:
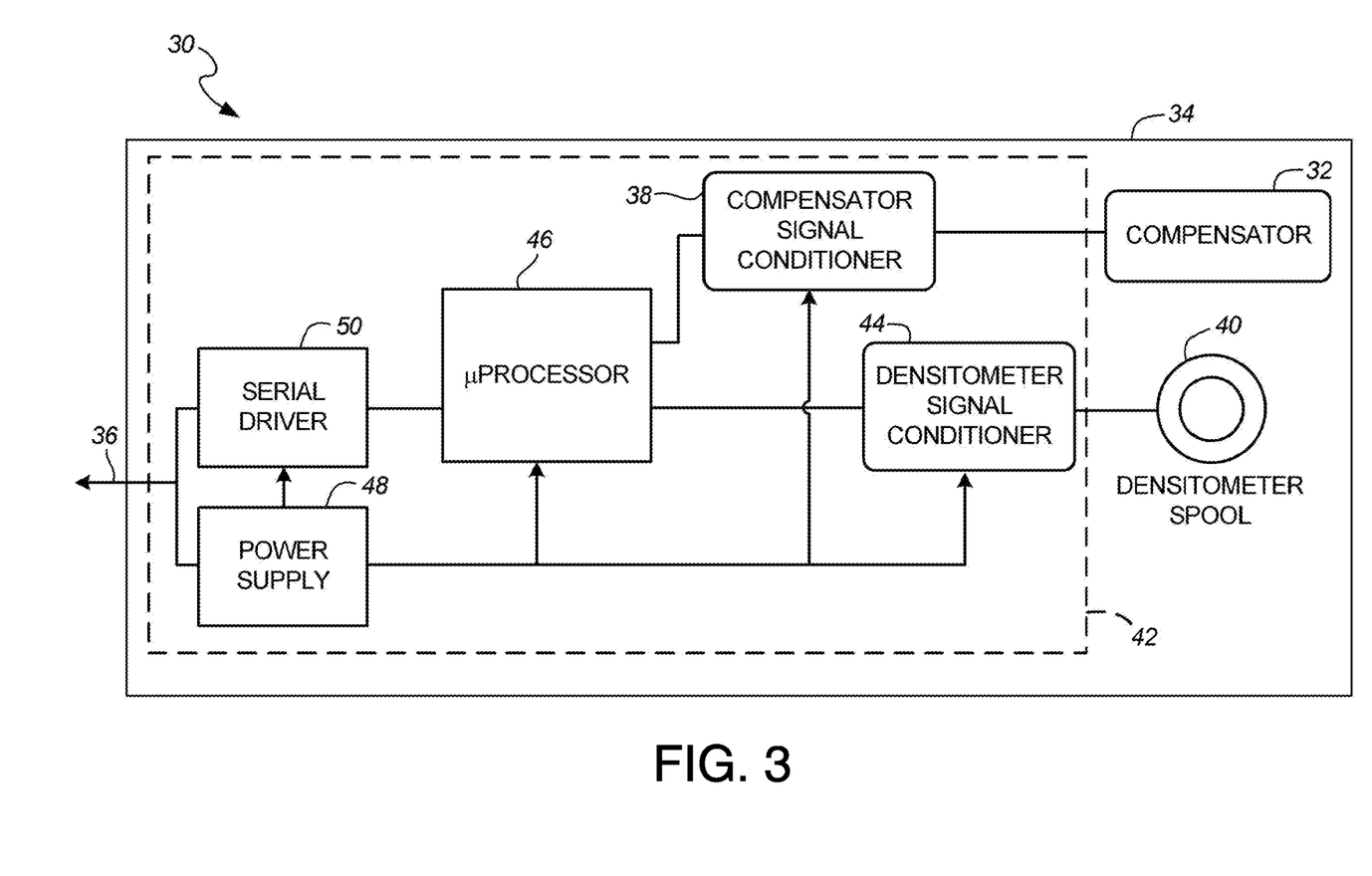
FIG. 3 is a block diagram of the integrated densitometer-compensator.
Figure 4:
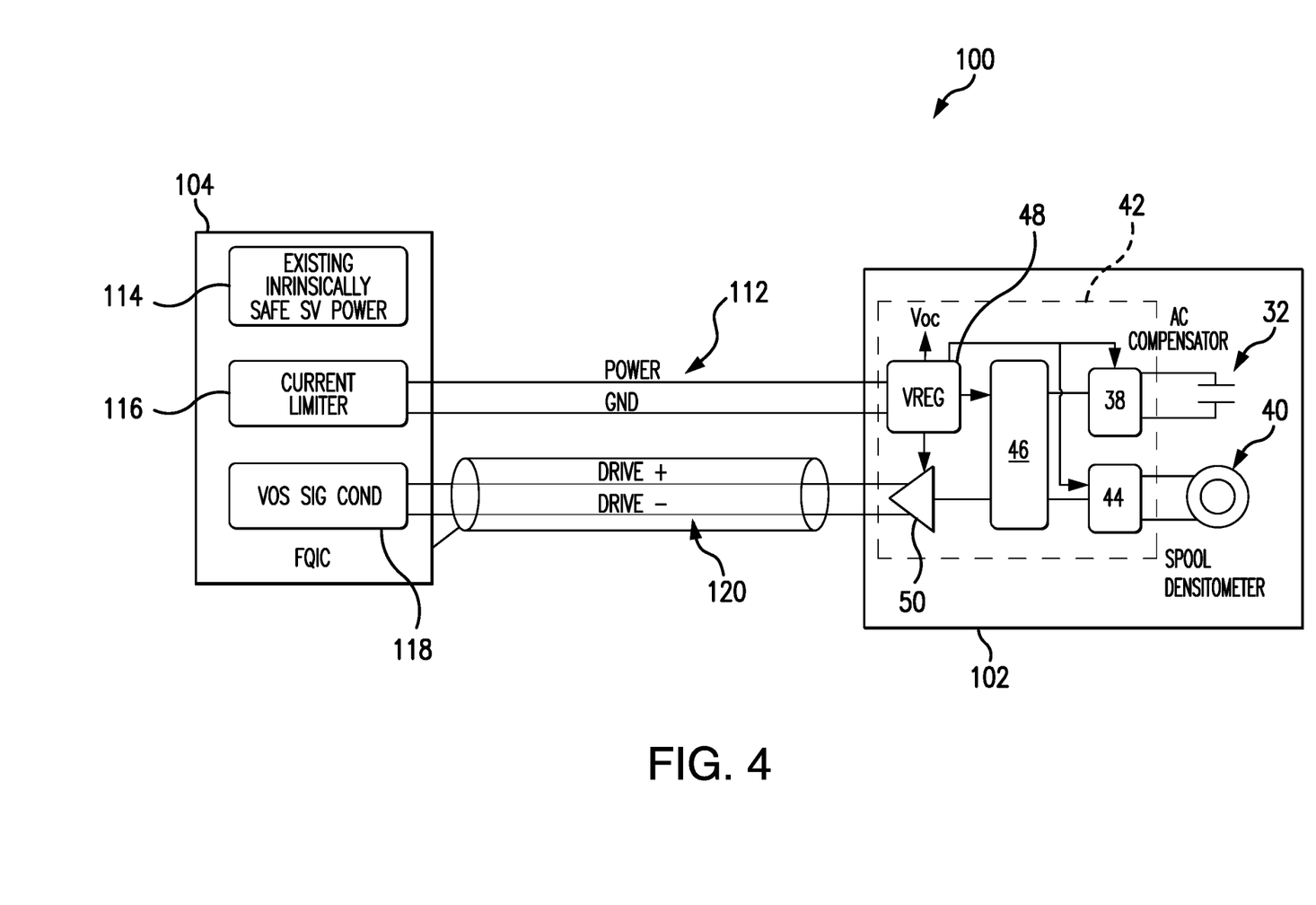
FIG. 4 is a block diagram of another embodiment of a fluid measurement system constructed in accordance with the present disclosure, showing a sensor system, e.g. an integrated densitometer-compensator, a processing system and an interface therebetween.

FIG. 3 is a block diagram of integrated densitometer-compensator 30 of FIG. 2. Shown in FIG. 3 are integrated densitometer-compensator 30, compensator 32, chassis 34, interface cable 36, compensator signal conditioner 38, densitometer 40, signal processor 42, densitometer signal conditioner 44, microprocessor 46, power supply 48, and serial driver 50. Signal processor 42 includes compensator signal conditioner 38, densitometer signal conditioner 44, microprocessor 46, power supply 48, and serial driver 50. It is contemplated that microprocessor 46 can include two discrete microprocessors, each corresponding to a respective one of densitometer signal conditioner 44 and compensator signal conditioner 38. Compensator 32 has an electrical capacitance value that varies with the dielectric value of fuel. Compensator signal conditioner 38 supplies an electrical signal to compensator 32 to measure the electrical capacitance value of compensator 32. In the embodiment illustrated in FIGS. 1A-3, compensator signal conditioner 38 produces an AC signal that has a frequency ranging from 6 KHz-18 KHZ, and amplitude ranging from 5-10 V p-p. In some embodiments the AC signal produced by compensator signal conditioner 38 can be lower in frequency than 6 KHz or higher in frequency than 18 KHz. In other embodiments the AC signal produced by compensator signal conditioner 38 can be lower in amplitude than 5 V p-p or higher in amplitude than 10 V p-p. In yet other embodiments compensator signal conditioner 38 can produce a non-AC signal that detects the electrical capacitance value of compensator 32.

Densitometer 40 is a vibrating mechanical spool that has a resonant frequency that varies with the density of the fuel being measured by integrated densitometer-compensator 30. Densitometer signal conditioner 44 includes an oscillator that drives densitometer 40 and a resonance detector circuit that maintains the resonant frequency of densitometer 40. As the density of the fuel surrounding densitometer 40 varies, the resonant frequency of densitometer 40 varies, and densitometer signal conditioner 44 adjusts the loop gain to maintain a resonant frequency while also producing a signal output that is representative of the fuel density. In the embodiment illustrated in FIGS. 1A-3, densitometer signal conditioner 44 can support self-resonance within the frequency range from 10-20 KHZ in densitometer 40. In some embodiments the frequency can be lower in frequency than 10 KHz or higher in frequency than 20 KHz. The performance and frequency response of densitometer 40 is highly dependent on the mechanical and physical properties of the particular densitometer 40 that is used in a particular embodiment. Because densitometer 40 includes a mechanically vibrating spool, normal variations that can occur in manufacturing processes can result in each particular embodiment of densitometer 40 having a frequency response function that is unique. Accordingly, densitometer 40 can include a resistor network (not shown) that is established during the manufacturing process of densitometer 40 that identifies the polynomial coefficients of the frequency response curve of densitometer 40 to densitometer signal conditioner 44. In the embodiment illustrated in FIGS. 1A-3, integrated densitometer-compensator 30 includes microprocessor 46 for digital signal processing. Accordingly, densitometer signal conditioner 44 can be programmed can be programmed with firmware values that provide a digital representation of the polynomial coefficients of the frequency response curve of densitometer 40. In the embodiment illustrated in FIGS. 1A-3, firmware values programmed into densitometer signal conditioner 44 provide the polynomial coefficients needed to represent the frequency response curve of densitometer 40, and a resistor network is not used.

Microprocessor 46 provides the signal processing for integrated densitometer-compensator 30. In the embodiment illustrated in FIGS. 1A-3, microprocessor 46 performs both analog and digital signal processing. Microprocessor 46 includes an analog-to-digital converter (ADC) that produces a digital representation of the electrical capacitance value produced by compensator signal conditioner 38. Microprocessor 46 also includes an analog-to-digital converter (ADC) that produces a digital representation of the fuel density value produced by densitometer signal conditioner 44. As described earlier, microprocessor 46 can also include firmware that is programmed with a digital representation of the polynomial coefficients of the frequency response curve of densitometer 40, for integrated densitometer-compensator 30 to provide an accurate representation of the density and dielectric value of fuel being measured. Microprocessor 46 can also include firmware and volatile and/or non-volatile memory for storing software, program instructions, compensation values, and other data that can be used by integrated densitometer-compensator 30. In some embodiments, microprocessor 46 can include a circuit board containing several electrical components including a commercially-available digital microprocessor, analog-to-digital converters (ADCs), firmware chips, volatile, and/or nonvolatile memory chips. In other embodiments, microprocessor 46 can include one or more application-specific integrated circuits (ASICs) without deviating from the scope of the present disclosure. Microprocessor 46 may also be abbreviated as μprocessor 46. All circuits that perform the signal processing for integrated densitometer-compensator 30 are within the scope of the present disclosure.

Power supply 48 provides electrical power to compensator signal conditioner 38, densitometer signal conditioner 44, microprocessor 46, and serial driver 50. In the embodiment illustrated in FIGS. 1A-3, power supply 48 receives power from avionics computer 28 via interface cable 36. In one embodiment, power supply 48 can receive electrical power from avionics computer 28, with interface cable 36 including a two-conductor wire pair. In this embodiment, power supply 48 conditions the received electrical power for distribution to the components within integrated densitometer-compensator 30 that require electrical power. The electrical power received from avionics computer 28 can be a direct current, an alternating current, or a hybrid waveform that conveys electrical power. The electrical power received from avionics computer 28 can be continuous or intermittent. Power supply 48 can also include an electrical energy storage device (not illustrated) that provides power to integrated densitometer-compensator 30 during periods when power is not being received from avionics computer 28. The electrical storage device can include, for example, a rechargeable electrochemical battery or an electrical capacitor.

In another embodiment, power supply 48 can receive optical power from avionics computer 28, with interface cable 36 including an optical fiber that transmits light. In this embodiment, power supply 48 can include an optical receptor cell (not illustrated) that converts optical power into electricity. The optical receptor cell can include one or more photovoltaic cells, or other devices, that convert optical power into electrical power. The optical power received from avionics computer 28 can be continuous or intermittent. Power supply 48 can also include an electrical energy storage (not illustrated) device that provides power to integrated densitometer-compensator 30 during periods when power is not being received from avionics computer 28. The electrical storage device can include, for example, a rechargeable electrochemical battery or an electrical capacitor.

In yet another embodiment, power supply 48 can include a long-life electrical storage device (not illustrated) that is charged at or after the time it is installed in integrated densitometer-compensator 30, and which powers integrated densitometer-compensator 30 for a span of time. A non-limiting example of a long-life electrical storage device is a lithium battery.

Serial driver receives 50 receives the digital representation of the fuel density and dielectric value that is measured by integrated densitometer-compensator 30 and transmits a serial data word to avionics computer 28 through interface cable 36. In one embodiment, serial driver 50 produces an electrical transmission of a serial data word with interface cable 36 including a two-conductor wire pair. The serial data word can also include an identifier for the particular integrated densitometer-compensator 30 producing the communication, thereby allowing for multiple integrated densitometer-compensators 30 to communicate with avionics computer 28 via interface cable 36. A single two-conductor wire pair can be used for transmitting electrical power from avionics computer 28 to integrated densitometer-compensator 30, and for transmitting the serial data word from integrated densitometer-compensator 30 to avionics computer 28. In one embodiment, the electrical serial data word transmission can occur simultaneously with the electrical power transmission by modulating the electrical power transmission. Non-limiting examples of electrical power modulation that can be used include frequency shift keying (FSK), amplitude shift keying (ASK), and phase shift keying (PSK). In another embodiment, the serial word transmission can occur periodically, with a timing protocol being used that allows alternating transmission of data and electrical power over interface cable 36. In yet another embodiment, a two-conductor wire pair can be used for transmitting electrical power from avionics computer 28 to integrated densitometer-compensator 30, and a different two-conductor wire pair can be used for transmitting the serial data word from integrated densitometer-compensator 30 to avionics computer 28. In the embodiment illustrated in FIGS. 1A-3, electrical shielding is not required on interface cable 36 because the signal processing occurs within integrated densitometer-compensator 30, and neither the power supply nor the serial word requires transmission within a shielded cable.

In another embodiment, serial driver 50 produces an optical transmission of a serial data word with interface cable 36 including an optical fiber. The serial data word can also include an identification code for the particular integrated densitometer-compensator 30 producing the communication, thereby allowing for multiple integrated densitometer-compensators 30 to communicate with avionics computer 28 via interface cable 36. In this embodiment, two or more integrated densitometer-compensators 30 can be daisy-chained together via interface cable 36.

In yet another embodiment, a single optical fiber can be used for transmitting optical power from avionics computer 28 to integrated densitometer-compensator 30, and for also transmitting the serial data word from integrated densitometer-compensator 30 to avionics computer 28. In one embodiment, the optical serial data word transmission can occur simultaneously with the optical power transmission by modulating the optical power transmission. Non-limiting examples of optical power modulation that can be used include frequency shift keying (FSK), amplitude shift keying (ASK), and phase shift keying (PSK). In another embodiment, a separate optical wavelength can be used for transmitting optical power and data over the same optical fiber. In yet another embodiment, the serial word transmission can occur periodically, with a timing protocol being used that allows alternating transmission of data and optical power over interface cable 36. In yet another embodiment, an optical fiber can be used for transmitting optical power from avionics computer 28 to integrated densitometer-compensator 30, and a different optical fiber can be used for transmitting the serial data word from integrated densitometer-compensator 30 to avionics computer 28.

Although an advantage of the present disclosure is to reduce the number of conductors on interface cable 36, thereby reducing the weight and cost associated with those conductors, benefit is still achieved in using two optical fibers because of the generally light weight and low cost of optical fibers as compared to using multiple shielded electrical cables.

In yet another embodiment, interface cable 36 can include both an optical fiber and a two-wire electrical pair. In this other embodiment, the optical fiber can be used for transmitting either optical power or the serial word, and the two-wire electrical pair can be used for transmitting the other.

The several embodiments described above refer to the electrical conductors within interface cable 36 as two-wire pairs. It should be appreciated that cables having more than two wires can perform the same function as described above, and are therefore within the scope of the present disclosure. For example, two two-wire pairs could be replaced with a four-wire cable, with equivalent results. Two two-wire pairs could also be replaced with a three-wire cable, in which one conductor is common to the other two, thereby achieving substantially similar results. In an alternative embodiment, a single wire electrical conductor could be used, with the fuel tank structure providing the electrical return path. Although this may not be a preferred embodiment in aviation systems, a single-wire conductor could be used with other applications of integrated densitometer-compensator 30.

In yet another embodiment, integrated densitometer-compensator 30 can be used without interface cable 36. In this embodiment, serial driver 50 can transmit the serial data word wirelessly utilizing any of a number of wireless signal transmissions including, without limitation, radio frequency, acoustical, and optical. In this embodiment, integrated densitometer-compensator 30 can be powered by an internal energy storage device and/or by a power supply that receives power wirelessly.

Integrated densitometer-compensator 30 was described in this disclosure using the example of wing fuel tanks 20 and center fuel tanks 22 being located with avionics computer 28 onboard aircraft 10, with this exemplary configuration not being limiting. For example, integrated densitometer-compensator 30 can be deployed anywhere it is desired to measure the density and dielectric value of a fluid, whether onboard an aircraft, other vehicle, or in a non-vehicle setting such as in an industrial setting. Moreover, the deployment of integrated densitometer-compensator 30 is not limited to closed tanks, but application can also be found within pipes and channels, and on open containers such as sumps and pits. Finally, any computing device can replace avionics computer 28, regardless of the type of computing device or the proximity between it and integrated densitometer-compensator 30. Integrated densitometer-compensator 30 can measure density with more accuracy than traditional inferential systems, e.g. integrated densitometer-compensator 30 can be a 1% of full mass improvement over traditional systems.

Another embodiment of a fluid measurement system 100 is shown in FIG. 4. System 100 includes a sensor system 102, which is substantially the same as integrated densitometer-compensator 30 and its various embodiments, described above. System 100 includes a processing system 104, which is resident in avionics computer 28 and its embodiments, described above. Processing system 104 can include many elements similar to those of avionics computer 28 and also includes a current limiter 116, which is described in more detail below. Elements of integrated densitometer 30 and avionics computer 28 can readily be incorporated into system 100 illustrated in FIGS. 4-6, and system 100 can readily be incorporated into aircraft 10 in a similar manner to that described above relative to integrated densitometer 30 and avionics computer 28.

As shown in FIG. 4, fluid measurement system 100 includes a power interface 112 between signal processor 42 and the processing system 104. Processing system 104 includes an intrinsically safe (IS) power source 114 and a current limiter 116. IS power source 114 is a +5V power rail and current limiter 116 operates at 25 mA and 50 µJ under normal operating conditions, at 50 mA and 200 µJ under fault and/or tank shorted conditions, and/or 125 mA and 200 µJ under lightning conditions. Current limiter 116 is positioned between IS power source 114 and power interface 112. Processing system includes an Input/Output (I/O) connector pin to connect with the power and ground conductors of interface 112. Processing system 104 includes a velocity of sound signal conditioner 118 to read and decode the serial word. System 100 includes data interface 120, e.g. a two-conductor wire pair 120, between signal processor 42 and the velocity of sound signal conditioner 118. Power interface 112 and data interface 120 are harnessed together as a single cable, e.g. similar to that of interface cable 36 and/or the other various embodiments thereof described above.

Figure 5:
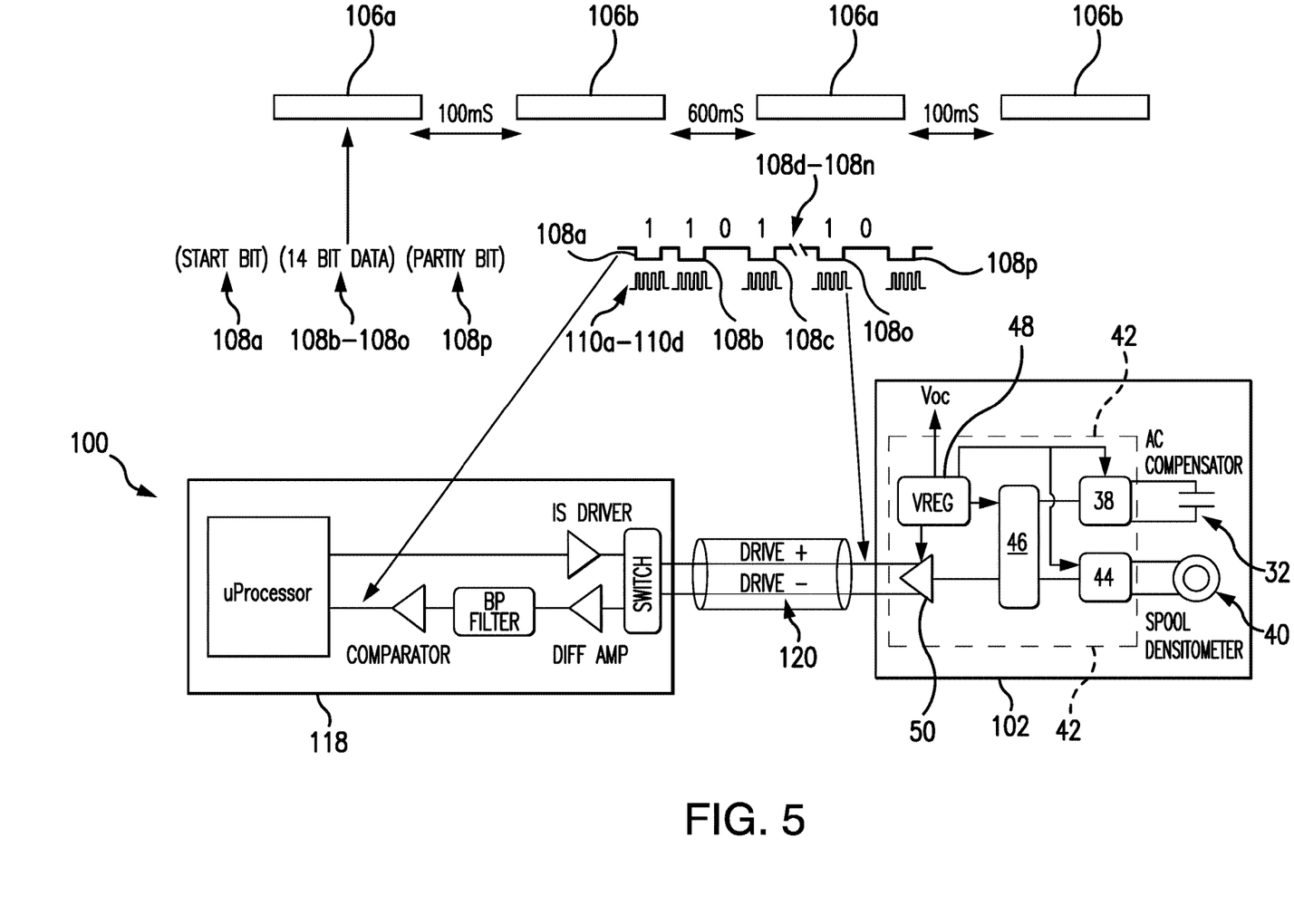
FIG. 5 is a block diagram of the interface assembly of FIG. 4, showing the serial word transmission between the sensor system and the processing system.

With reference now to FIGS. 4-5, sensor system 102 includes a signal processor 42, like signal processor 42 of FIGS. 1A-3, described above. Sensor system 102 produces a serial word that represents the density and dielectric value of fuel being measured by sensor system 102 via the AC compensator 32 and the spool densitometer 40. Signal processor 42 includes compensator a signal conditioner 38, a densitometer signal conditioner 44, a microprocessor 46, a power supply 48, and serial driver 50. In conjunction with densitometer signal conditioner 44, microprocessor 46 configured and adapted to produce a serial word 106a that is indicative of a density and, in conjunction with compensator a signal conditioner 38 is configured and adapted to produce a serial word 106b that is indicative of a capacitance of the fluid. Together, serial word 106a indicative of density and serial word 106b indicative of capacitance make up a pair. Each pair of words 106a/106b is separated by approximately 600 microseconds, in some embodiments. Each word in a given pair, in some embodiments, is separated by 100 microseconds. For example, the second word, e.g. 106b, in the pair is separated from the first word, e.g. 106a by approximately 100 microseconds. Each serial word 106a/106b includes a plurality of bits 108. Each bit 108 is a 1 MHz bit 108 cluster 108a having four 1 MHz pulses 110a-110d. While shown as having four pulses, those skilled in the art will readily appreciate that each bit cluster can include a plurality of 1 MHz pulses. For example, four to eight pulses. The plurality of bits 108 include a start bit 108a, a plurality of data bits 108b-o, and a parity bit 108p. Processing system 104 is operatively connected to signal processor 42 to read the serial words 106a/106b and decode the serial words 106a/106b. Processing system 104 can include software that replaces the inferred density value traditionally provided by a velocity of sound signal conditioner 118 with a density measurement from densitometer 40.

Accordingly, each individual sensor system 102, e.g. each integrated densitometer-compensator, can include a unique address, allowing for two or more integrated densitometer-compensators 102 to be daisy-chained together along a single data interface 120, as described above. In other embodiments, integrated densitometer-compensator 102 can wirelessly transmit the serial words 106a/106b (including a unique address) to a wireless receiving device (not shown), which is connected to processing system 104. As used in this disclosure, "serial word" is used to describe a digital serial data stream being transmitted by integrated densitometer-compensator 102, with this data stream including digital representations of the density and dielectric value of fuel being measured by integrated densitometer-compensator 102. Under some operating conditions, integrated densitometer-compensator 102 can transmit a serial word that represents only the density or the dielectric value of the fuel. Under other operating conditions, integrated densitometer-compensator 102 can transmit a serial word that provides data other than the density or the dielectric value of the fuel. The "serial word" may also include a device address, checksum bits, and any other data, and it may be of any word size.

Figure 6:
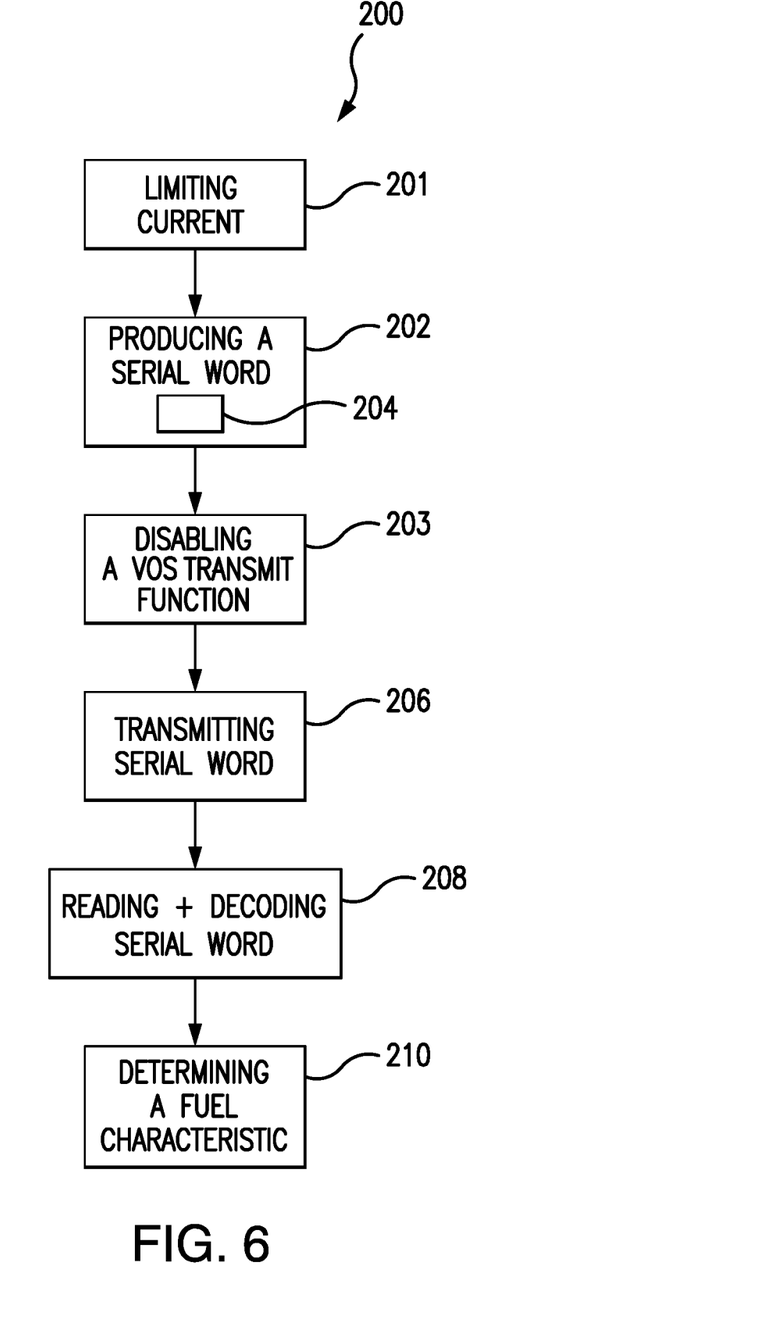
FIG. 6 is a flow chart schematically depicting an embodiment of a method for transmitting a fluid characteristic between the sensor system and the processing system in accordance with the present disclosure.

As shown in FIG. 6, a method 200 for transmitting a fluid characteristic between a sensor system, e.g. sensor system 102, and a processing system, e.g. processing system 104, includes producing a serial word that is indicative of a fluid characteristic value with a signal processor, e.g. signal processor 42, as indicated schematically by box 202. Before producing the serial word, a first signal can be generated with a first device, e.g. compensator a signal conditioner 38, that is indicative of the dielectric value of the fluid (as measured by compensator 32) and a second signal with a second device, e.g. densitometer signal conditioner 44, that is indicative of the density of the fluid (as measured with densitometer 40). The signal processor then produces a digital signal in the form of a serial word that is indicative of the dielectric value and the density of the fluid, based on the first signal and the second signal. The method includes disabling a velocity of sound (VOS) transmit function of the VOS signal conditioner, e.g. VOS signal conditioner 118, as indicated schematically by box 203, in order to eliminate signal bus contention on the drive (e.g. data interface 120) an allow for improved communication between the VOS signal conditioner and the signal processor. No transmission from the VOS signal conditioner to the signal processor would be required in conjunction with the sensor system. The receiving function of the VOS is still enabled in order to receive and read the serial word, described in more detail below. Producing the serial word includes generating a plurality of bits with the signal processor, as indicated schematically by box 204. Each bit is a 1 MHz bit cluster, e.g. bit cluster 108a-108p. Each bit cluster includes a plurality of 1 MHz pulses, e.g. four pulses 110a-110d. The plurality of bits include a start bit, e.g. start bit 108a, a plurality of data bits, e.g. data bits 108a-108o, and a parity bit, e.g. parity bit 108p.

Once generated, the method 200 includes transmitting the serial word externally of the signal processor, as indicated schematically by box 206. The method includes reading and decoding the serial word with the velocity of sound signal conditioner of the processing system, as indicated schematically by box 208. Method 200 includes determining a fuel characteristic, e.g. the density, capacitance, and, ultimately, the fuel mass, as indicated schematically by box 210. The method 200 includes limiting current to 50 mA or less and 200 μJ with a current limiter, e.g. current limiter 116, as indicated schematically by box 201. The method can also include limiting energy storage components in the sensor system to 4 μF based on 5 V potential. Method 200 can also include updating the software of the processing system such that the fuel mass calculation replaces the inferred density value traditionally provided by a velocity of sound signal conditioner with the density measurement from a densitometer, e.g. densitometer 40.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Discussion of Possible Embodiments

The following are non-exclusive descriptions of possible embodiments of the present invention. A system for determining the dielectric value and a density of a fluid according to an exemplary embodiment of this disclosure, among other possible things, includes a first device configured to produce a first signal that is indicative of the dielectric value of the fluid; a second device configured to produce a second signal that is indicative of the density of the fluid; and a signal processor in operable communication with both the first device and the second device, the signal processor configured to calculate a digital signal that is indicative of the dielectric value and the density of the fluid that can be communicated externally of the signal processor.

The system of the preceding paragraph can optionally include, additionally and/or alternatively, any one or more of the following features, configurations and/or additional components:

A further embodiment of the foregoing system, wherein the first device is comprised of a compensator configured to produce an electrical capacitance signal that is indicative of the dielectric value of the fluid and a compensator signal conditioner electrically connected to the compensator, configured to produce an electrical signal that is indicative of the electrical capacitance signal; the second device is comprised of a densitometer spool configured to produce a mechanical response that is indicative of the density of the fluid and a densitometer signal conditioner electromagnetically connected to the densitometer spool, configured to produce an electrical signal that is indicative of the mechanical response; and the signal processor is comprised of a microprocessor configured to store a plurality of correction factors representing the mechanical response and calculate the digital signal that is representative of the dielectric value and the density of the fluid, and a serial driver configured to produce a serial word that is representative of the digital signal and modulate a carrier signal wherein the modulated carrier signal is representative of the serial word.

A further embodiment of the foregoing system, further comprising a power supply, the power supply configured to provide electrical power to the compensator signal conditioner, the densitometer signal conditioner, the microprocessor, and the serial driver.

A further embodiment of the foregoing system, further comprising an energy storage device, wherein the energy storage device is configured to store electrical energy.

A further embodiment of the foregoing system, further comprising a data interface, the data interface configured to transmit the serial word.

A further embodiment of the foregoing system, wherein the power supply is configured to: receive electrical input power via the power interface; convert the electrical input power into electrical power; and provide the electrical power to the compensator signal conditioner, the densitometer signal conditioner, the microprocessor, and the serial driver.

A further embodiment of the foregoing system, wherein the power supply is configured to: receive optical input power via the power interface; convert the optical input power into electrical power; and provide the electrical power to the compensator signal conditioner, the densitometer signal conditioner, the microprocessor, and the serial driver.

A further embodiment of the foregoing system, wherein the data interface is comprised of a two-wire electrical pair; the serial driver is configured to transmit the serial word over the two-wire electrical pair; and the power supply is configured to receive electrical input power over the two-wire electrical pair.

A further embodiment of the foregoing system, wherein the serial driver is configured to transmit the serial word wirelessly.

A further embodiment of the foregoing system, wherein the data interface is comprised of an optical fiber; the serial driver is configured to transmit the serial word over the optical fiber;

and the power supply is configured to receive optical input power over the optical fiber.

A further embodiment of the foregoing system, wherein the serial driver is configured to transmit the serial word utilizing digital encoding selected from the group consisting of: frequency shift keying, amplitude shift keying, phase shift keying.

A further embodiment of the foregoing system, wherein the serial driver is configured to transmit the serial word utilizing a first wavelength of light; and the power supply is configured to receive optical input power utilizing a second wavelength of light.

A further embodiment of the foregoing system, wherein the serial driver has an identification code, and the serial word further comprises the identification code.

A system for measuring a dielectric value and a density of a fluid in a tank, the system comprising: a remote computing device; a first device configured to produce a first signal that is indicative of the dielectric value of the fluid; a second device configured to produce a second signal that is indicative of the density of the fluid; and a signal processor electrically connected to both the first device and the second device, the signal processor configured to produce a first electrical signal that is representative of the first signal, produce a second electrical signal that is representative of the second signal, calculate a digital signal that is representative of the dielectric value and the density of the fluid, produce a serial word that is indicative of the digital signal, and modulate a carrier signal, wherein the modulating is representative of the serial word; a power supply configured to receive power input from the remote computing device; and an data interface configured to: transmit the serial word to the remote computing device and transmit input power from the remote computing device to the power supply.

The system of the preceding paragraph can optionally include, additionally and/or alternatively, any one or more of the following features, configurations and/or additional components:

A further embodiment of the foregoing system, wherein the interface further comprises a two-wire pair; and the power supply is configured to receive electrical power input from the remote computing device via the two-wire pair; and the signal processor is configured to transmit the serial word to the remote computing device via the two-wire pair.

A further embodiment of the foregoing system, wherein the interface cable further comprises an optical fiber; and the power supply is configured to receive optical power input from the remote computing device via the optical fiber; and the signal processor is configured to transmit the serial word to the remote computing device via the optical fiber.

A further embodiment of the foregoing system, wherein the signal processor is configured to transmit the serial word utilizing digital encoding selected from the group consisting of: frequency shift keying, amplitude shift keying, phase shift keying.

A further embodiment of the foregoing system, wherein the signal processor is configured to transmit the serial word utilizing a first wavelength of light; and the power supply is configured to receive optical input power utilizing a second wavelength of light.

A method for determining a dielectric value and a density of a fluid within a tank comprising the steps of: producing, via a first device disposed at the tank, a first signal indicating the dielectric value of the fluid; producing, via a second device disposed at the tank, a second signal indicating the density of the fluid; calculating, in a signal processor disposed at the tank, a digital signal that is indicative of the dielectric value and the density of the fluid, based on the first signal and the second sign; and transmitting the digital signal externally of the signal processor.

The method of the preceding paragraph can optionally include, additionally and/or alternatively, any one or more of the following features, configurations and/or additional components:

A further embodiment of the foregoing method, further comprising producing, by the signal processor, a serial word that is representative of the digital signal; modulating, by the signal processor, a carrier signal, wherein the modulated carrier signal is representative of the serial word; and transmitting, by an interface cable, the modulated carrier signal.

A fluid measurement system, among other possible things, includes a signal processor and a processing system. The signal processor is configured and adapted to produce a serial word that is indicative of a fluid characteristic that is configured to be communicated externally of the signal processor. The processing system is operatively connected to the signal processor to read the serial word and decode the serial word.

The system of the preceding paragraph can optionally include, additionally and/or alternatively, any one or more of the following features, configurations and/or additional components:

A further embodiment of the foregoing system, wherein the serial word is representative of at least one of a density or a capacitance of a fluid.

A further embodiment of the foregoing system, wherein the serial word includes a plurality of bits. Each bit can be a 1 MHz bit cluster.

A further embodiment of the foregoing system, wherein the plurality of bits includes a start bit, a plurality of data bits, and a parity bit.

A further embodiment of the foregoing system, wherein each 1 MHz bit cluster includes a plurality of 1 MHz pulses.

A further embodiment of the foregoing system, wherein the system includes a power interface between the signal processor and the processing system.

A further embodiment of the foregoing system, wherein the processing system includes an intrinsically safe power source and a current limiter.

A further embodiment of the foregoing system, wherein the current limiter is between the intrinsically safe power source and the power interface.

A further embodiment of the foregoing system, wherein the processing system includes a velocity of sound signal conditioner to read and decode the serial word.

A further embodiment of the foregoing system, wherein the system includes a two-conductor wire pair between the signal processor and the velocity of sound signal conditioner.

A method for transmitting a fluid characteristic between a sensor system and a processing system includes producing a serial word that is indicative of a fluid characteristic value with a signal processor. The method includes transmitting the serial word externally of the signal processor. The method includes reading and decoding the serial word with a processing system to determine the fluid characteristic value.

A further embodiment of the foregoing method, wherein producing the serial word includes generating a plurality of bits with the signal processor.

A further embodiment of the foregoing method, wherein the plurality of bits include a start bit, a plurality of data bits, and a parity bit. Each bit can be a 1 MHz bit cluster, and/or each bit cluster can include a plurality of 1 MHz pulses.

A further embodiment of the foregoing method, wherein the method includes limiting current to 50 mA or less with a current limiter between an intrinsically safe power source and a power interface.

A further embodiment of the foregoing method, wherein the reading and decoding of the serial word is done by a velocity of sound signal conditioner of the processing system.

A further embodiment of the foregoing method, wherein the method includes disabling a velocity of sound transmit function of the velocity of sound signal conditioner.

A further embodiment of the foregoing method, wherein transmitting the serial word includes wirelessly transmitting the serial word from the signal processor to the processing system.

The methods and systems of the present disclosure, as described above and shown in the drawings provide for a sensor system and processing system with superior properties including easier install, reduced cost and minimal downtime. While the apparatus and methods of the subject disclosure have been shown and described with reference to certain embodiments, those skilled in the art will readily appreciate that change and/or modifications may be made thereto without departing from the scope of the subject disclosure.

What is claimed is:

1. A fluid measurement system, the system comprising:
at least one of AC compensator configured and adapted to measure a capacitance of a fluid or a spool densitometer configured and adapted to measure a density of the fluid;
a signal processor operatively connected to at least one of the AC compensator or the spool densitometer, the signal processor configured and adapted to produce a serial word that is indicative of at least one of the density of the fluid from the spool densitometer or the capacitance of the fluid from the AC compensator, the serial word configured to be communicated externally of the signal processor; and
a processing system operatively connected to the signal processor to read the serial word and decode the serial word, wherein the processing system includes a velocity of sound signal conditioner to read and decode the serial word, wherein a transmit function of the velocity of sound signal conditioner is configured and adapted to be disabled to allow for improved communication between the velocity of sound signal conditioner and the signal processor.

2. The system as recited in claim 1, wherein the serial word includes a plurality of bits, wherein each bit is a 1 MHz bit cluster.

3. The system as recited in claim 2, wherein each 1 MHz bit cluster includes a plurality of 1 MHz pulses.

4. The system as recited in claim 1, wherein the serial word includes a plurality of bits, wherein the plurality of bits include a start bit, a plurality of data bits, and a parity bit.

5. The system as recited in claim 4, wherein each bit is a 1 MHz bit cluster.

6. The system as recited in claim 5, wherein each bit cluster includes a plurality of 1 MHz pulses.

7. The system as recited in claim 1, wherein the system includes a power interface between the signal processor and the processing system.

8. The system as recited in claim 7, wherein the processing system includes an intrinsically safe power source and a current limiter, wherein the current limiter is between the intrinsically safe power source and the power interface.

9. The system as recited in claim 1, wherein the processing system includes
a two-conductor wire pair between the signal processor and the velocity of sound signal conditioner.

10. A method for transmitting a fluid characteristic between a sensor system and a processing system, the method comprising:
disabling a velocity of sound transmit function of a velocity of sound signal conditioner;
producing a serial word that is indicative of at least one of a density of a fluid or a capacitance of the fluid with a signal processor;
transmitting the serial word externally of the signal processor; and
reading and decoding the serial word with the velocity of sound signal conditioner of a processing system to determine the fluid characteristic value.

11. The method as recited in claim 10, wherein producing the serial word includes generating a plurality of bits with the signal processor, wherein each bit is a 1 MHz bit cluster.

12. The method as recited in claim 11, wherein each bit cluster includes a plurality of 1 MHz pulses.

13. The method as recited in claim 12, wherein producing the serial word includes generating a plurality of bits with the signal processor, wherein the plurality of bits include a start bit, a plurality of data bits, and a parity bit.

14. The method as recited in claim 13, wherein each bit is a 1 MHz bit cluster.

15. The method as recited in claim 14, wherein each 1 MHz bit cluster includes a plurality of 1 MHz pulses.

16. The method as recited in claim 10, further comprising limiting current to 50 mA or less with a current limiter between an intrinsically safe power source and a power interface.

17. The method as recited in claim 10, wherein transmitting the serial word externally includes wirelesly transmitting the serial word from the signal processor to the processing system.

* * * * *